United States Patent [19]

Jasenak

[11] Patent Number: 4,900,760
[45] Date of Patent: Feb. 13, 1990

[54] FLEXIBLE POLYURETHANE FOAM PREPARED FROM A NOVEL POLYISOCYANATE MIXTURE

[75] Inventor: James R. Jasenak, Sewickley, Pa.
[73] Assignee: Mobay Corporation, Pittsburgh, Pa.
[21] Appl. No.: 307,651
[22] Filed: Feb. 7, 1989

Related U.S. Application Data

[62] Division of Ser. No. 62,933, Jun. 16, 1987, Pat. No. 4,822,517.

[51] Int. Cl.$^4$ ............................................. C08G 18/73
[52] U.S. Cl. ....................................................... 521/160
[58] Field of Search ........................................ 521/160

[56] References Cited

U.S. PATENT DOCUMENTS

| | | | |
|---|---|---|---|
| 3,344,162 | 9/1967 | Rowton et al. | 560/347 |
| 3,362,979 | 1/1968 | Bentley | 560/359 |
| 3,676,497 | 7/1972 | Recchia et al. | 564/333 |
| 3,960,788 | 6/1976 | Cuscurida et al. | 521/160 |
| 4,113,014 | 9/1978 | Kubens et al. | 166/295 |
| 4,162,357 | 7/1979 | Kubens et al. | 528/67 |
| 4,163,095 | 7/1979 | Kubens et al. | 528/67 |
| 4,237,240 | 12/1980 | Jarre et al. | 521/159 |
| 4,251,639 | 2/1981 | Jarre et al. | 521/159 |
| 4,256,849 | 3/1981 | Ick et al. | 521/129 |
| 4,261,852 | 4/1981 | Carroll et al. | 528/59 |
| 4,365,025 | 12/1982 | Murch et al. | 521/159 |
| 4,448,904 | 5/1984 | Dominguez | 521/160 |
| 4,506,040 | 3/1985 | Raes et al. | 252/182 |
| 4,650,899 | 3/1987 | Kervennal et al. | 252/182 |
| 4,668,734 | 5/1987 | Dietrich et al. | 252/182 |

*Primary Examiner*—Harold D. Anderson
*Assistant Examiner*—Dennis R. Daley
*Attorney, Agent, or Firm*—Joseph C. Gil; Richard E. L. Henderson

[57] ABSTRACT

The present invention is directed to a novel isocyanate mixture and the use thereof in producing a flexible polyurethane foam. The polyisocyanate mixture comprises
(a) for 73 to 77% by weight of methylene bis(phenylisocyanate), said methylene bis(phenylisocyanate) having an isomer content as follows:
 (i) from about 30 to about 34% by weight of the 2,4' isomer,
 (ii) from about 60 to about 66% by weight of the 4,4'-isomer, and
 (iii) from about 3 to about 7% by weight, the 2,2' isomer, the percent of said isomers totaling 100%
(b) from 23 to 27% by weight of higher functional methylene-bridged polyphenyl polyisocyanates, the percents of components (a) and (b) totaling 100%, and wherein said polyisocyanate mixture has an isocyanate group content of from about 30 to about 33.5 percent by weight.

1 Claim, No Drawings

FLEXIBLE POLYURETHANE FOAM PREPARED FROM A NOVEL POLYISOCYANATE MIXTURE

This is a division of Ser. No. 062,933, filed 6/16/87, now U.S. Pat. No. 4,822,517.

BACKGROUND OF THE INVENTION

Polyisocyanate mixtures containing methylene bis(phenylisocyanate) and higher functional methylene-bridged polyphenyl polyisocyanates are known. It is also known that the amount of the various isomers of methylene bis(phenylisocyanate) can vary over a wide range. For example, U.S. Pat. No. 3,344,162 describes the production of aromatic polyisocyanates containing from about 50 to about 95 percent by weight of the diisocyanate, of which from about 10 to about 95 percent by weight is the 2,4'-isomer. U.S. Pat. No. 3,362,979 describes a polyisocyanate mixture containing from 20 to 100% by weight of the diisocyanate, of which 20 to 95 percent by weight is the 2,4'-isomer. U.S. Pat. No. 3,676,497 describes the preparation of an amine mixture (which can subsequently be phosgenated to prepare the corresponding isocyanate) containing diamines and higher functional amines, where the diamine portion consists of from about 15 to about 85 percent by weight of the 4,4'-isomer, from about 10 to about 60 percent by weight of the 2,4'-isomer, and from about 5 to about 25 percent by weight of the 2,2'-isomer.

U.S. Pat. No. 3,960,788 describes the use of a polymethylene polyphenyl polyisocyanate in the production of a rigid isocyanurate foam. The isocyanate used had an average functionality of from about 2.1 to about 2.4 and consisted of a mixture of (i) from about 60 to about 75% by weight of methylene diphenylisocyanate, said methylene diphenylisocyanate having an isomer content as follows:
  (a) from about 60 to about 90% by weight of the 4,4'-isomer,
  (b) from about 18 to about 33% by weight of the 2,4'-isomer, and
  (c) from about 2 to about 7% by weight of the 2,2'-isomer, and
(ii) from about 25 to about 40% by weight of higher functionality methylene-bridged polyphenyl-polyisocyanates.

The preferred isocyanate had a diisocyanate content of about 67% with the 4,4'-, 2,4'- and 2,2'-isomer contents being about 74%, about 22%, and about 4% respectively.

Additionally, several patents describes various uses for high 2,4'-isomer content isocyanates. See, e.g., U.S. Pat. Nos. 4,113,014, 4,162,357, 4,163,095, 4,261,852 and 4,448,904.

U.S. Pat. No. 4,256,849 describes the use of a mixture of isocyanates based on methylene bis(phenylisocyanate) to produce flexible polyurethane foams. The isocyanate mixture is described as having a 4,4'-diisocyanate content of from 60 to 90% by weight, a 2,4'-diisocyanate content of from 3 to 30% by weight, and a higher functional methylene bridged isocyanate content of from 0 to 37% by weight. Finally, a variety of other isocyanate mixtures based on methylene-bis(phenylisocyanate) have been described in the art. See, e.g., U.S. Pat. Nos. 4,237,240, 4,251,639 and 4,365,025.

While foams prepared from the isocyanate mixtures of the prior art are satisfactory for many applications, such foams may be too firm for other applications. Additionally, the processing of the foams of the prior art in many cases is not acceptable.

DESCRIPTION OF THE INVENTION

The present invention is directed to a novel isocyanate mixture and the use thereof to produce a flexible polyurethane foam. The use of the novel isocyanate mixture to prepare flexible polyurethane foams leads to improved processing and to foams having good load-bearing properties.

More particularly, the present invention is directed to a polyisocyanate mixture comprising (a) from 73 to 77 % by weight of methylene bis(phenylisocyanate), preferably from 74 to 76% by weight, said methylene bis(phenylisocyanate) having an isomer content as follows:
  (i) from about 30 to about 34 % by weight of the 2,4'-isomer,
  (ii) from about 60 to about 66 % by weight of the 4,4'-isomer, and
  (iii) from about 3 to about 7 % by weight of the 2,2'-isomer, the percents of said isomers totaling 100%, and
(b) from 23 to 27 % by weight of higher functional methylene-bridged polyphenyl polyisocyanates, the percents of components a) and b) totalling 100%, said polyisocyanate mixture having an isocyanate group content of from about 30 to about 33.5 percent by weight.

The presently preferred isocyanate mixtures contain 75% by weight of methylene bis(phenylisocyanate) having an isomer distribution of from about 4 to about 7% by weight 2,2'-isomer, from about 21 to about 33% by weight of the 2,4'-isomer and from about 60 to 65% by weight of the 4,4'-isomer. The preferred mixtures have isocyanate group contents of from 32 to 33% by weight.

The isocyanate mixture can be prepared directly by any of the methods known and used in the art. (See, e.g., the prior art cited in the Background of the Invention). Alternatively, the mixtures can be produced by blending the various components to yield the desired ratio of components. The presently preferred method is to blend various isomer content polyisocyanates to arrive at the necessary mixtures.

The isocyanate mixtures of the present invention are used to make flexible polyurethane foam using techniques and materials generally known and used in the art. The resultant foam has good load bearing properties and good processing properties.

The invention is further illustrated but is not intended to be limited by the following examples in which all parts and percentages are by weight unless otherwise specified.

EXAMPLES

Foam samples were produced on a Mobay Hennecke HK-100 high pressure two component foam machine utilizing impingement type mixing metered through hydraulically operated injection nozzles. Reactants were supplied to the nozzle from pressurized and temperature controlled jacketed vessels by Bosch vertical piston pumps. The pumps were driven by dual speed D.C. motors. The nozzles were opened by hydrophobic oil pressure. Nozzle operating pressures were in the range of from 1000 to 2500 psi. Mixing took place in an 8mm self-cleaning MQ mixhead. The materials were charged into a heated aluminum box mold measuring 15"×15"×4" and allowed a residence time of 4 minutes before removing from the mold. Foams were evaluated for processing (cell openness) by observing the lid rise height upon releasing the top lid, and also by the degree of hand crushing required to open the foam cells, if necessary.

Physical properties were measured 24 hours after demold and were conducted utilizing ASTM D3574-77.

The method used to qualify process as bad or good was taken from observations and values assigned as to the ease or difficulty in crushing to prevent foams from shrinking. The lower overall values the better the foam. The values assigned were:
(1) Totally Open—no crushing required—no shrinking.
(2) Slightly tight—foams need crushing but normal handling upon demold sufficient to effect crushing.
(3) Extremely tight—foams would split internally upon demold and created excessive pressure in the mold cavity.

The formulations and results were as indicated in the following Table (all parts are by weight)

The materials used were as follows:
(i) POLYOL A: a glycerine/propylene oxide/ethylene oxide polyether containing primary hydroxy groups and having an OH number of 28 (weight ratio of propylene oxide to ethylene oxide of about 87:13).
(ii) POLYOL B: a sorbitol/propylene oxide/ethylene oxide reaction product having an OH number of about 70 (weight ratio of propylene oxide to ethylene oxide of about 12:88).
(iii) A-1: Niax A-1— a tertiary amine catalyst available from Union Carbide and consisting of about 70% by weight of bis(2-di-methylaminoethyl)ether and 30% by weight of glycols.
(iv) A-4: Niax A-4— a tertiary amine catalyst available from Union Carbide.
(v) 33LV: DABCO 33LV— a 33% by weight solution of triethylene diamine in dipropylene glycol, available from Air Product Corporation.
(vi) 9224: a commercially available surfactant mixture of low molecular weight siloxanes available from Mobay Corporation.

TABLE

| EXAMPLE | 1* | 2* | 3 | 4 | 5 | 6 |
|---|---|---|---|---|---|---|
| Polyol A | 100 | 100 | 100 | 100 | 100 | 100 |
| Polyol B | 1.0 | 1.0 | 1.0 | 1.0 | 1.0 | 1.0 |
| A-1 | 0.18 | 0.18 | 0.18 | 0.18 | 0.18 | 0.18 |
| A-4 | 0.45 | 0.45 | 0.45 | 0.45 | 0.45 | 0.45 |
| 33LV | 0.18 | 0.18 | 0.18 | 0.18 | 0.18 | 0.45 |
| 9224 | 0.5 | 0.5 | 0.5 | 0.5 | 0.5 | 0.5 |
| Water | 3.0 | 3.0 | 3.2 | 3.2 | 3.5 | 3.5 |
| Iso | 49.15 | 39.32 | 52.0 | 41.6 | 56.28 | 45.02 |
| Iso Index | 100 | 80 | 100 | 80 | 100 | 80 |
| Iso Used: | | | | | | |
| Monomer content | 68.89 | 68.89 | 75 | 75 | 75 | 75 |
| 2,2'-isomer | 3.4% | 3.4% | 7.1% | 7.1% | 4.5% | 4.5% |
| 2,4'-isomer | 31.3% | 31.3% | 33.2% | 33.2% | 30.9% | 30.9% |
| 4,4'-isomer | 65.3% | 65.3% | 59.7% | 59.7% | 64.6% | 64.6% |
| % NCO | 32.8% | 32.8% | 32.8% | 32.8% | 32.8% | 32.8% |
| Processing | BAD | BAD | GOOD | GOOD | GOOD | GOOD |
|  | 3 | 3 | 1 | 2 | 1 | 2 |
| Density pcf | 3.0 | 3.5 | 3.0 | 3.5 | 3.0 | 3.5 |
| IFD 25% R | 46 | 36 | 57 | 35 | 63 | 39 |
| 50% Comp Set | 8.3 | 6.2 | 4.2 | 5.2 | 4.5 | 5.6 |
| 75% Comp Set | 8.0 | 6.3 | 8.1 | 9.3 | 8.0 | 8.8 |

*Comparative Examples

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A flexible polyurethane foam prepared by a process comprising reacting an isocyanate with an active-hydrogen-containing material in the presence of a blowing agent, wherein the isocyanate is a polyisocyanate mixture comprising
   (a) from 73 to 77 % by weight of methylene bis(phenylisocyanate), said methylene bis(phenylisocyaante) having an isomer content of
      (i) from about 30 to about 34 % by weight of the 2,4' isomer,
      (ii) from about 60 to about 66 % by weight of the 4,4' isomer, and
      (iii) from about 3 to about 7 % by weight of the 2,2' isomer, the percent of said isomers totaling 100%;
   (b) from 23 to 27 % by weight of higher functional methylene-bridged polyphenyl polyisocyanates, the percents of components a) and b) totaling 100%, and wherein said polyisocyanate mixture has an isocyanate group content of from about 30 to about 33.5 percent by weight.

* * * * *